United States Patent
Yoon et al.

(10) Patent No.: US 9,714,892 B2
(45) Date of Patent: Jul. 25, 2017

(54) WEAR TESTING MACHINE

(71) Applicant: Caterpillar Inc., Peoria, IL (US)

(72) Inventors: Hyung K. Yoon, Peoria, IL (US); Eric Kelsey, Hennepin, IL (US)

(73) Assignee: Caterpillar Inc., Peoria, IL (US)

( * ) Notice: Subject to any disclaimer, the term of this patent is extended or adjusted under 35 U.S.C. 154(b) by 260 days.

(21) Appl. No.: 14/473,259

(22) Filed: Aug. 29, 2014

(65) Prior Publication Data
US 2016/0061703 A1 Mar. 3, 2016

(51) Int. Cl.
*G01N 3/56* (2006.01)
*G01N 33/30* (2006.01)

(52) U.S. Cl.
CPC .............. *G01N 3/56* (2013.01); *G01N 33/30* (2013.01)

(58) Field of Classification Search
CPC .................................. G01N 3/56; G01N 33/30
USPC .......................................................... 73/9, 10
See application file for complete search history.

(56) References Cited

U.S. PATENT DOCUMENTS

| | | |
|---|---|---|
| 3,946,593 A | 3/1976 | Ruget |
| 5,388,442 A | 2/1995 | Kumar et al. |
| H1998 H * | 11/2001 | Cameron .................... 73/114.79 |
| 2003/0140707 A1* | 7/2003 | Pyle .......................... G01N 3/56 73/808 |
| 2008/0168823 A1* | 7/2008 | Maassen .................... G01N 3/56 73/7 |

FOREIGN PATENT DOCUMENTS

| | | | |
|---|---|---|---|
| GB | 2108274 A | | 5/1983 |
| GB | 2194060 A | | 2/1988 |
| JP | 62293140 A | * | 12/1987 |
| JP | 06308016 A | * | 11/1994 |

OTHER PUBLICATIONS

Machine translation of JP06-308016.*

* cited by examiner

*Primary Examiner* — David M Gray
*Assistant Examiner* — Andrew V Do
(74) *Attorney, Agent, or Firm* — Leydig, Voit & Mayer, LTD.

(57) ABSTRACT

To simulate various rolling and sliding conditions, a wear testing machine can include a load roller arrangement having at least a first load roller, a second load roller, and a third load roller arranged in a triangular layout. A test roller can be disposed between and in simultaneous contact with the first, second, and third load rollers along at least three points of contact. The load rollers and the test roller can be configured to rotate with respect to each other at a same rotational speed or at different rotational speeds. In an embodiment, the wear testing machine can introduce lubricant to the points of contact between the three load rollers and the test roller.

17 Claims, 6 Drawing Sheets

WEAR TESTING MACHINE

TECHNICAL FIELD

This patent disclosure relates generally to the field of tribology and, more particularly, to a wear testing machine for simulating wear conditions between moving components.

BACKGROUND

In mechanics, different components often move in contact with respect to each other to transmit power or motion; tribology is the study of this topic. One example of moving components may be the rotation of engaged gears and, more particularly, the relative motion of the intermeshing teeth of the gears. As is known, relative motion between interacting components may result in friction and wear. Friction and the resulting wear depend upon the load conditions and relative velocity of the components and can be classified according to different characteristics. Examples of wear characteristics include adhesion in which the minute contact points create localized adhesive bonds that destructively detach when relative motion occurs and abrasion in which asperities of one surface cut through the other surface. To reduce friction and wear, lubrication is often provided between the moving components. Many different types of lubrication exist including greases, oils, and dry lubricants such as powdered graphite. Different lubricants have different characteristics and may come in different grades and, accordingly, some lubricants may be better suited for certain conditions than other lubricants.

To test the wear conditions and/or the suitability of various lubricants for those conditions, a test apparatus may be constructed to simulate the relative motion of parts. One example of a test apparatus is disclosed in U.S. Pat. No. 5,388,442 ("the '442 patent"), assigned to Tranergy Corp. The '442 patent describes a machine which includes a powered wheel and a freely rotating wheel which are placed adjacent each other in a single point of contact along their circular surfaces. The powered wheel can be driven by a motor to rotate with respect to the free wheel, the rotation of which may be adjustably constrained by a brake to mimic various rolling and/or sliding conditions. Lubrication can be introduced between the wheels and a load cell while transducers, visual inspection, and the like can measure its affect. The present disclosure is also directed to a machine for simulating different load and wear conditions and/or testing lubricants.

SUMMARY

The disclosure describes, in one aspect, a wear testing machine that includes a plurality of load rollers including at least a first load roller, a second load roller, and a third load roller. The first load roller, second load roller and third load roller can be disposed in a triangular arrangement with each other and can be configured to each rotate around a respective axis line. A test roller can be disposed between and in simultaneous rolling/sliding contact with the first load roller, the second load roller, and the third load roller. To simulate rolling and or sliding contact between the components, the test roller is rotatable with respect to the load rollers.

In another aspect, the disclosure describes a method of wear testing for, by way of example, tribology purposes. The method provides a load roller arrangement including a first load roller, a second load roller, and a third load roller arranged in a triangular layout. The first load roller can be configured to articulate with respect to the second and third load rollers. According to the method, a test roller can be disposed between and in contact with the first load roller, the second load roller, and the third load roller with at least three points of contact. To simulate wear conditions, the method rotates the first load roller, second load roller, and third load roller with respect to the test roller.

In yet another aspect of the disclosure, there is described a wear testing machine having a load roller arrangement including a plurality of load rollers configured to rotate about a respective plurality of axis lines. The wear testing machine further includes a test roller disposed partially within the load roller arrangement such that the test roller makes at least three points of rolling/sliding contact with the plurality of load rollers of the load roller arrangement.

DETAILED DESCRIPTION

Figure 1:
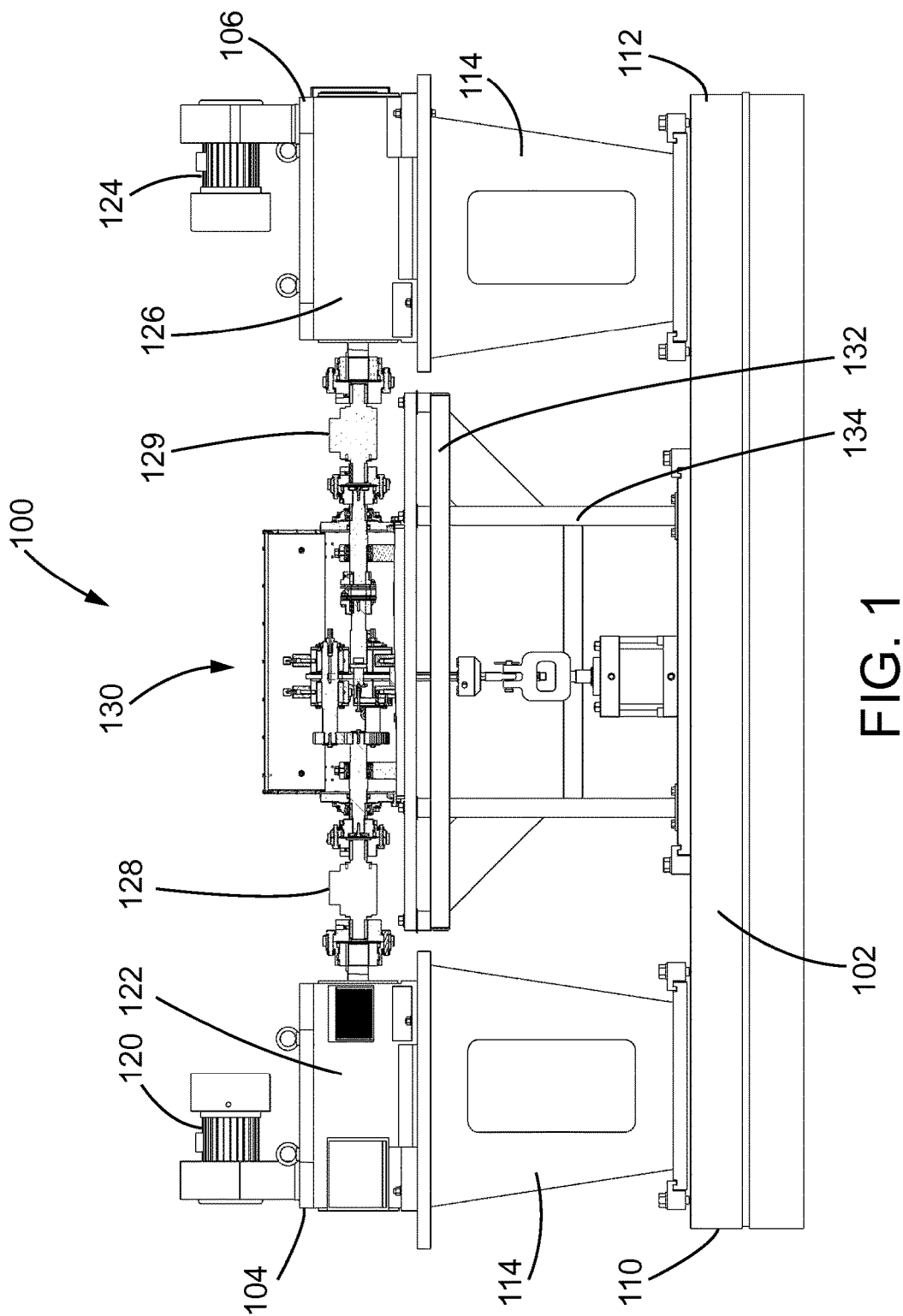
FIG. 1 is perspective view of a wear testing machine according to the disclosure and, in particular embodiment shown, a three roller machine including a roller apparatus disposed between first and second drive units for simulating different load and wear conditions and/or for testing lubricants.

This disclosure relates to a wear testing machine for simulating motion and wear between interacting components and/or for testing the affect of lubricants used to reduce friction and wear. However, it will be appreciated that the disclosed machine may have other applications beyond those described herein and that particular modes of use are not to be construed as limitations unless explicitly stated in a claim. Referring now to the figures, wherein like reference numbers refer to like elements, there is disclosed in FIG. 1 a wear testing machine 100 and, more particularly, an embodiment of a three roller machine. To support the other components, the wear testing machine 100 can include a longitudinal platform 102 arranged horizontally on which those other components can be mounted. Other components can include a first drive unit 104 and a second drive unit 106 arranged in an opposing manner with the first drive unit disposed toward a first edge 110 of the longitudinal platform and the second drive unit disposed toward a second edge 112 of the platform. Each of the first and second drive units 104, 106 can be mounted on a respective support stand 114 that may be in the form of a four-legged steel or metal truss that elevates the drive units with respect to the longitudinal platform 102, though, in other embodiments, the support stands can be eliminated.

To provide motive power that drives the wear components of the wear testing machine 100, the first drive unit 104 can include a first drive motor 120 operatively associated with a first gear box 122 and the second drive unit 106 can likewise include a second drive motor 124 operatively associated with a second gear box 126. The first and second drive motor 120, 124 can be any suitable size and type of electric motor for producing rotational motion such as three-phrase, single-phase, alternating current, direct current, or have any other suitable characteristic. In other embodiments, the drive units 104, 106 can operate on alternative power. The first and second gear boxes 122, 126 can include a plurality of gears for increasing or reducing torque and/or speed output by the drive motors 120, 124. Protruding from the first gear box 122 can be a first driveshaft 128 and protruding from the second gear box 126 can be a second driveshaft 129. The first driveshaft 128 and second driveshaft 129 can protrude toward each other and, in various embodiments, the first and second driveshafts can be axially aligned with each other.

Figure 2:
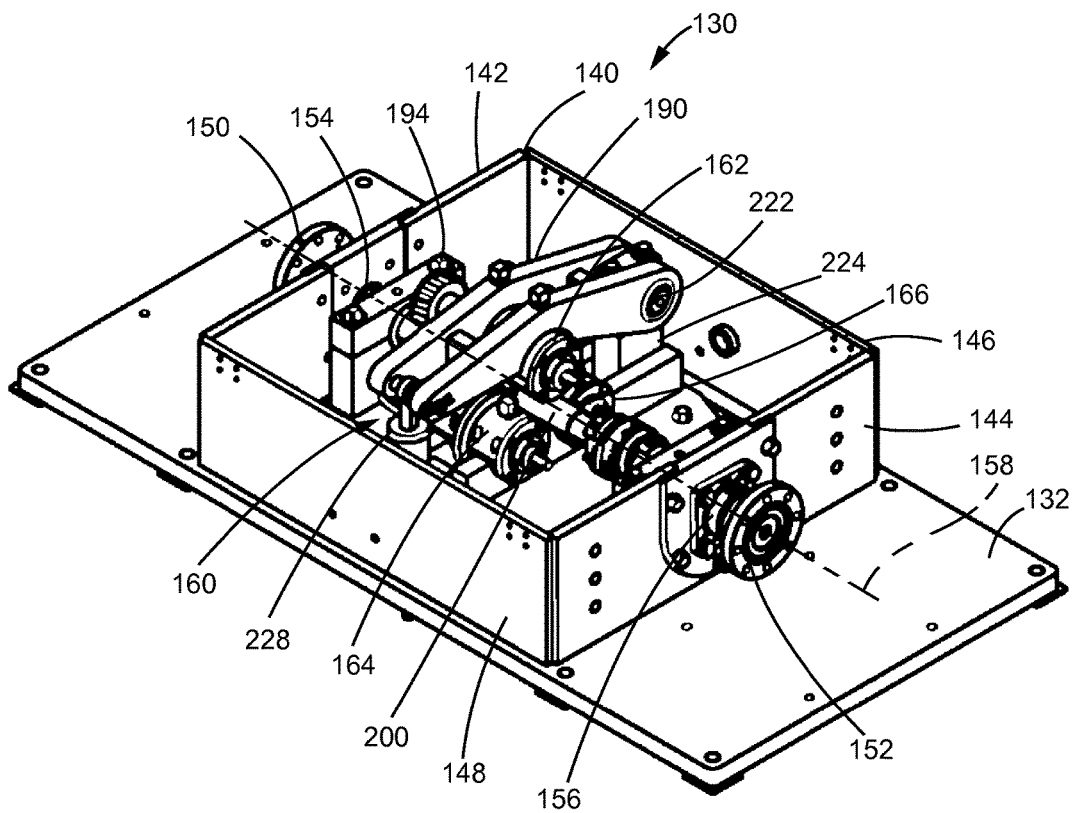
FIG. 2 is a top perspective view of the test unit of the wear testing machine showing the arrangement of the three load rollers for rotation with respect to a test roller disposed between them.
Figure 3:
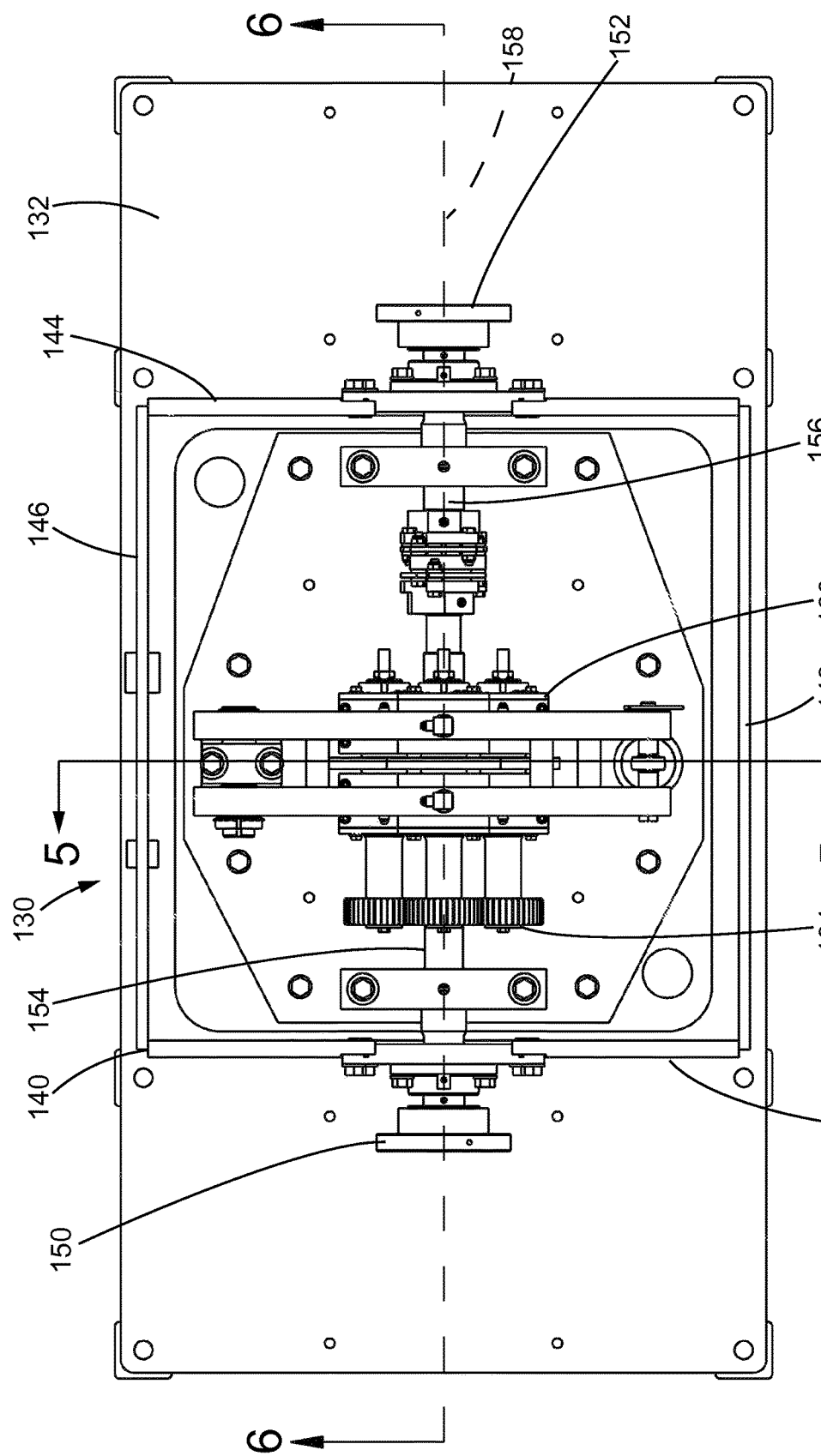
FIG. 3 is a top plan view of the test unit showing the alignment of the load roller arrangement with respect to the test roller and a gear train interconnecting the three load rollers for controlled rotation.

Disposed between the first and second drive units 104, 106 can be a test unit 130 wherein the actual simulation of relative motion occurs. The test unit 130 can be mounted on a horizontal base 132 that is supported in an elevated position over the longitudinal platform 102 by another support stand 134 so as to be level with the first and second drive units 104, 106. The table-like support stand 134 can likewise have four vertical legs extending between the horizontal base 132 and the longitudinal platform 102. Referring to FIGS. 2 and 3, the test unit 130 can include an enclosure 140 that delineates a compartment for housing the components that interact with each other to simulate the friction and wear conditions. In the illustrated embodiment, the enclosure 140 can be rectangular and can include a first sidewall 142, a second sidewall 144 parallel to and opposite of the first sidewall, and parallel third and fourth sidewalls 146, 148 extending perpendicularly between and interconnecting the first and second sidewalls. The enclosure 140 can extend vertically from the horizontal base 132. Although not shown, in various embodiments, the enclosure 140 can include a cover that can be placed atop the interconnected sidewalls. Within the enclosure 140, conditions such as temperature and/or humidity can be controlled.

Referring still to FIGS. 2 and 3, to transmit power in the form of rotary motion from the first and second drive units into the test unit 130, a first drive flange 150 can protrude from the first sidewall 142 of the enclosure 140 and a second drive flange 152 can protrude from the second sidewall 144. The first and second drive flanges 150, 152 can couple to the respective first and second driveshafts by, for example, thread fasteners that secure the drive flanges to similar structures on the driveshafts. The first drive flange 150 can be mounted on a first roller shaft 154 that extends into the first sidewall 142 and the second drive flange 152 likewise extends into the second sidewall 144. The first and second roller shafts 154 and 156 can be rotatably supported within the sidewalls 142, 144 by ball bearings, journal bearings, hydrodynamic bearings, bushings, or the like. Like the first and second drive shafts, the first and second roller shafts 154, 156 can be aligned with respect to each other within the boxlike enclosure 140 along an axis line 158.

Figure 4:
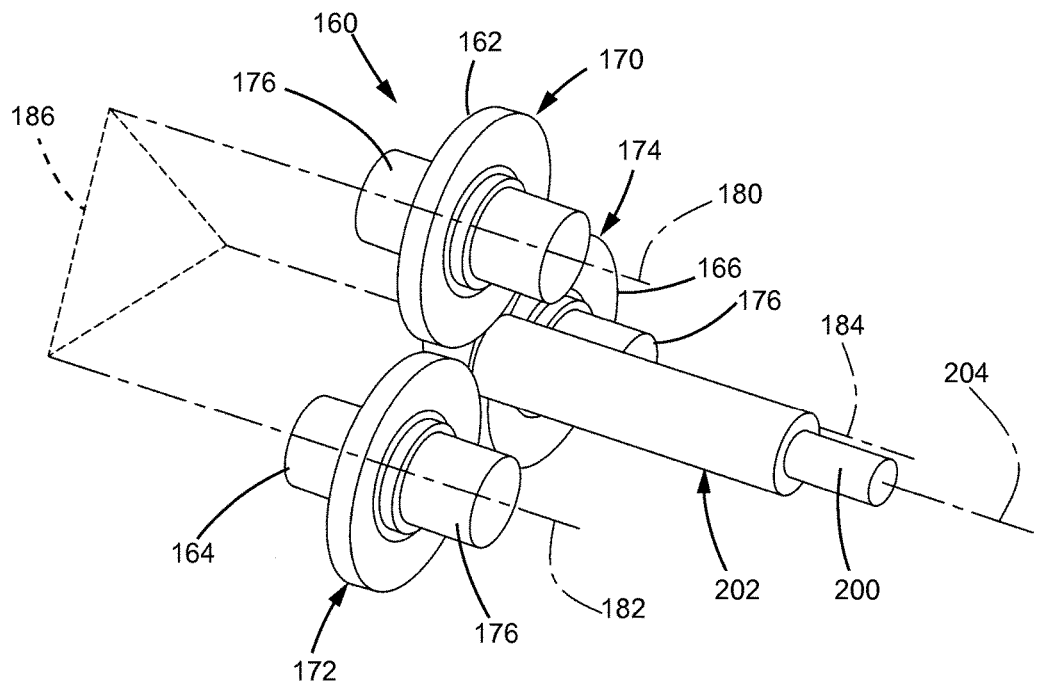
FIG. 4 is detailed perspective view of the three load rollers removed from the test unit in a triangular layout and engaging the test roller.

Referring to FIGS. 2 and 4, disposed inside the enclosure 140 and operatively coupled, directly or indirectly, with the first roller shaft 154 can be a load roller arrangement 160 that applies a load to a test piece placed in the test unit 130 causing friction and/or wear to be imparted to the test piece. The load roller arrangement 160 can include at least a first load roller 162, a second load roller 164, and a third load roller 166. The first load roller 162 can be circular or cylindrical in shape such that it has a curved or circular first peripheral surface 170 and may delineate a first axis line 180 around which the first peripheral surface can rotate. The second load roller and the third load roller can likewise have a respective second and third peripheral surface 172, 174 that are rotatable about respective second and third axis lines 182, 184. The load rollers can be made from any suitable material for wear testing such as, for example, iron, steel, or aluminum. Moreover, the first, second, and third peripheral surfaces 170, 172, 174 of the respective load rollers can be profiled or crowned so as to mitigate high edge loading and to have a relative degree of surface roughness. For example, the profiling or crowning can be on the order of 40 microns, but other surface roughness dimensions may be suitable for other experiments.

Figure 5:
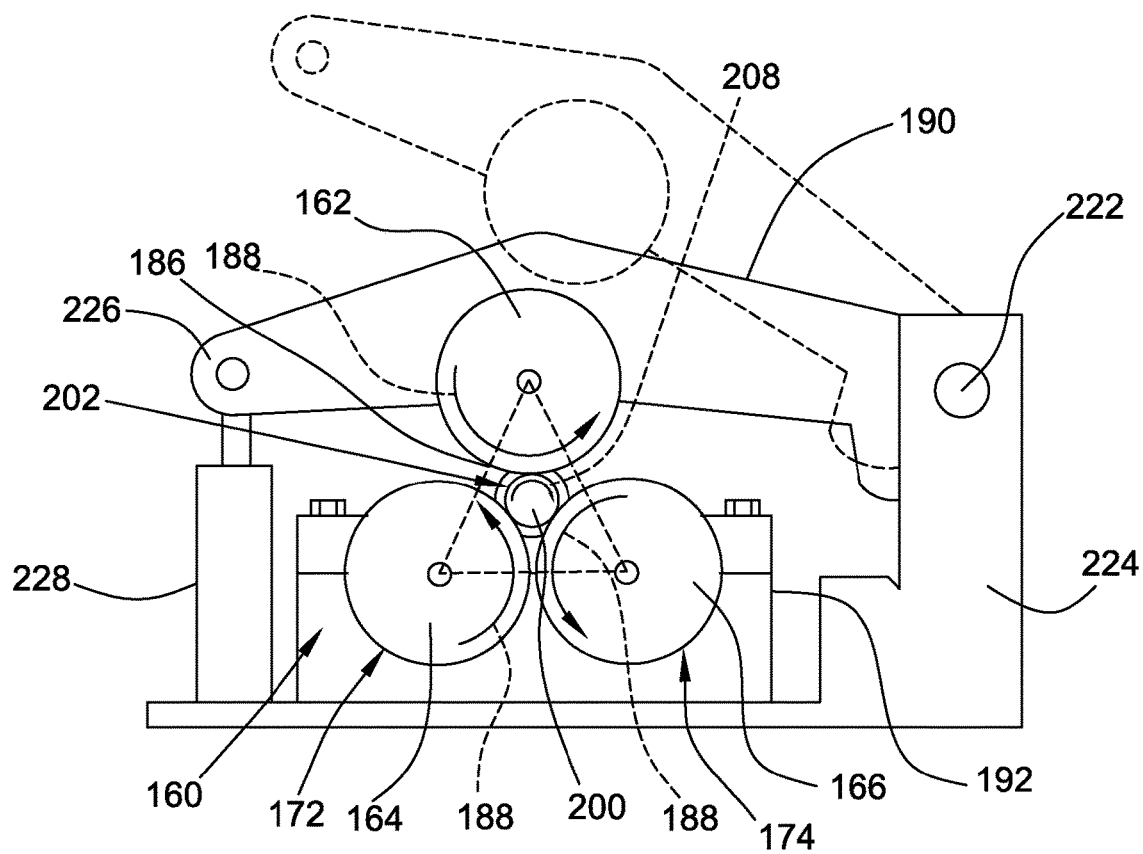
FIG. 5 is a cross-sectional schematic taken along line 5-5 of FIG. 3 depicting the rotational interaction between the three load rollers and the test roller and an articulating load arm extending over the load roller arrangement.

As illustrated in FIGS. 4 and 5, within the load roller arrangement 160, the first load roller 162, second load roller 164, and third load roller 166 can be closely packed together to form a generally triangular layout. In particular, the first axis line 180, second axis line 182, and third axis line 184 can be parallel with each other and the first peripheral surface 170, second peripheral surface 172, and third peripheral surface 174 are in close proximity with each other. In this arrangement, the first load roller 162, second load roller 164, and third load roller 166 from a triangular layout 186, as generally indicated by the imaginary triangle interconnecting each of the axis lines 180, 182, 184. In the illustrated embodiment, the triangular layout 186 is in the form of an equilateral triangle with each angle measuring 60° but, in other embodiments, the load rollers can be arranged in different layouts. Although in the illustrated embodiment, the load rollers have a disk-like shapes with the circular peripheral surfaces 170, 172, 174 extending around centrally disposed hubs 176 aligned along the respective axis lines 180, 182, 184, in other embodiments, the load rollers can have different shapes.

As indicated by the arrows 188 in FIG. 5, the first, second, and third load rollers 162, 164, 166 can be configured to rotate with respect to each other. To enable the first load roller 162 to rotate, it can be rotatably supported by a load arm 190 that extends horizontally over the load roller arrangement 160 and that has an angled camber or bend wherein the first load roller is accommodated. To enable the second and third load rollers 164, 166 to rotate, they may be supported in pillow blocks or bearing blocks 192 disposed toward the bottom of the test unit. The load arm 190 and bearing blocks 192 can maintain the rotatable load rollers at their respective fixed positions corresponding to the corners of the triangular layout 186. Any suitable types of bearings can be used to support the load rollers including, for example, ball bearings, roller bearings, and/or fluid bearings. In the illustrated embodiment, the first, second, and third load rollers 162, 164, 166 are depicted by the arrows 188 as each rotating in the counterclockwise direction. However, it will be appreciated that in other embodiments, they may rotate in the clockwise direction or in different directions with respect to each other. Further, because the load rollers rotate in the same counterclockwise direction in the illustrated embodiment, a small clearance spacing can be maintained between the first, second, and third peripheral surfaces 170, 172, 174. However, in other embodiments, the first, second, and third load rollers 162, 164, 166 can be adjacent to each other and the first, second, and third peripheral surfaces 170, 172, 174 can be configured to be in rolling contact with each other.

Referring back to FIGS. 2 and 3, to rotatably drive the three load rollers of the load roller arrangement 160, a gear train 194 is located in the enclosure 140 of the test unit 130 proximate the first sidewall 142 that operably connects the first roller shaft 154 with the load roller arrangement. The gear train 194 can include a plurality of engaging gears that distribute the rotating motion input from the first drive flange 150 and the first roller shaft 154 to each of the load rollers. Accordingly, the first drive unit can drive the load rollers together in a common manner at fixed respective; speeds. However, in other embodiments, individual drive units or different drive configurations can be used. Further, as stated above, the gear train 194 can be configured to rotate the three load rollers 162, 164, 166 in the same or different directions.

To conduct testing in accordance with the disclosure, a test piece in the form of a test roller 200 can be disposed in the test unit 130 to frictionally engage with the load roller arrangement 160. As illustrated in FIGS. 2 and 4, the test roller 200 can be an elongated, cylindrical shaped object having a cylindrical exterior surface 202 delineating another axis line 204. The test roller 200 can be made from any suitable material appropriate for the type of testing being done including, for example, iron, steel, and/or aluminum. Although the cylindrical exterior surface 202 typically is smooth, under some testing conditions it may demonstrate various degrees of surface roughness. Referring to FIGS. 4 and 5, the test roller 200 can be positioned within and centered between the triangular layout 186 of the first, second, and third load rollers 162, 164, 166 so as to be in surface contact with the first, second, and third peripheral surfaces 170, 172, 174. In this particular arrangement, the test roller forms three separate points of contact along its cylindrical exterior surface 202, one point of contact associated with each of the three load rollers. Moreover, the axis line 204 of the test roller 200 is generally parallel with the axis lines 180, 182, 184 of the three load rollers. In the illustrated embodiment, the test roller 200 can have a diameter substantially less than the larger diameter of the load rollers to enable it to fit within the triangular layout but in other embodiments can have a different relative diameter. Additionally, the length of the test roller can be substantially longer than the load rollers so that the test roller adequately protrudes into the load roller arrangement.

Referring to FIG. 5, to simulate loading or contact conditions of applications such as engagement of gears, the first, second, and third load rollers 162, 164, 166 can be rotated relative to each other in a manner that imparts rolling or sliding contact to the test roller 200. In particular, the surface-to-surface contact between the load roller arrangement 160 and the test roller 200 can wear down the cylindrical exterior surface 202 of the test roller over time. As known to those of skill in the tribology art, when surfaces are in moving contact with each other, the surfaces may wear or be otherwise affected because of frictional and/or loading forces occurring between them. Examples of wear include abrasion in which a harder surface removes material of a softer counterface and adhesion wherein localized intimate contact between surfaces generates adhesive bonds that relative motion of the surfaces break removing material. Other surface effects can include rippling, pitting, indentation, distortion, delamination, fatigue, and the like. The disclosed wear testing machine can simulate these effects on the test roller allowing for materials testing, lubricant studies, failure mode studies, and the like. Crowning or profiling the peripheral surfaces 170, 172, 174 of the load rollers can enhance the rate or degree of wear of the test roller 200.

Figure 6:
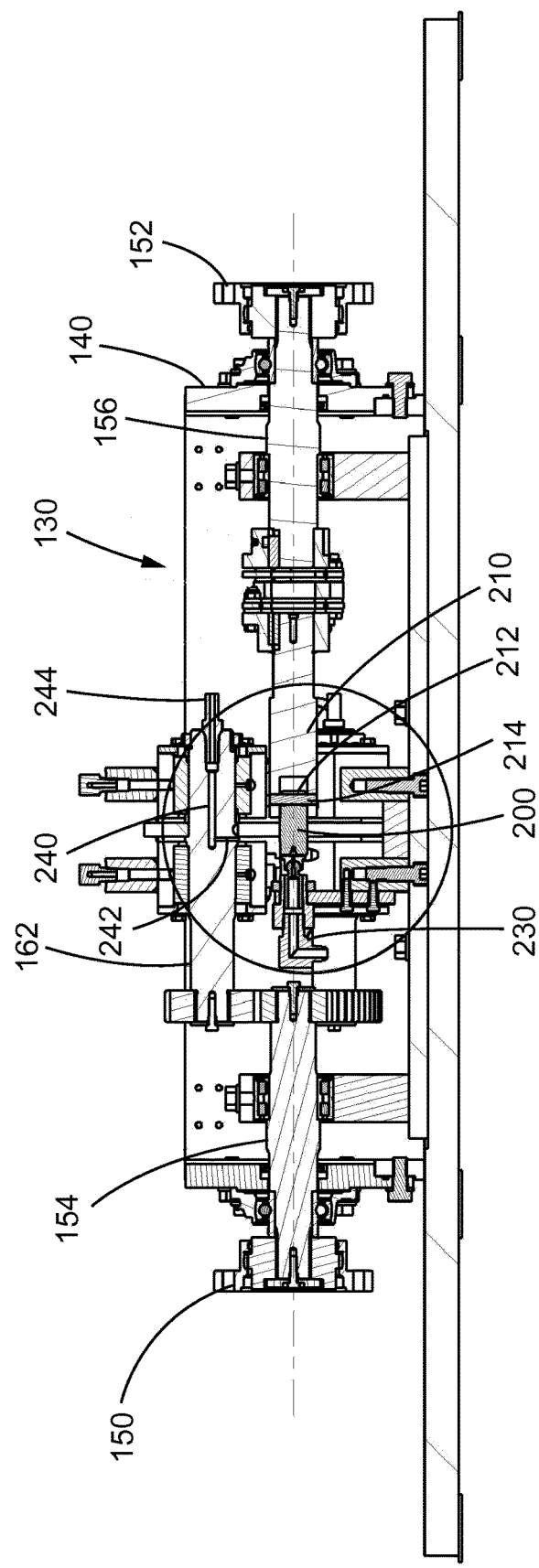
FIG. 6 is an elevational cross-sectional view of the test unit taken along line 6-6 of FIG. 3 showing the alignment of first driveshaft and the second driveshaft for driving the load roller arrangement and the test roller respectively.
Figure 7:
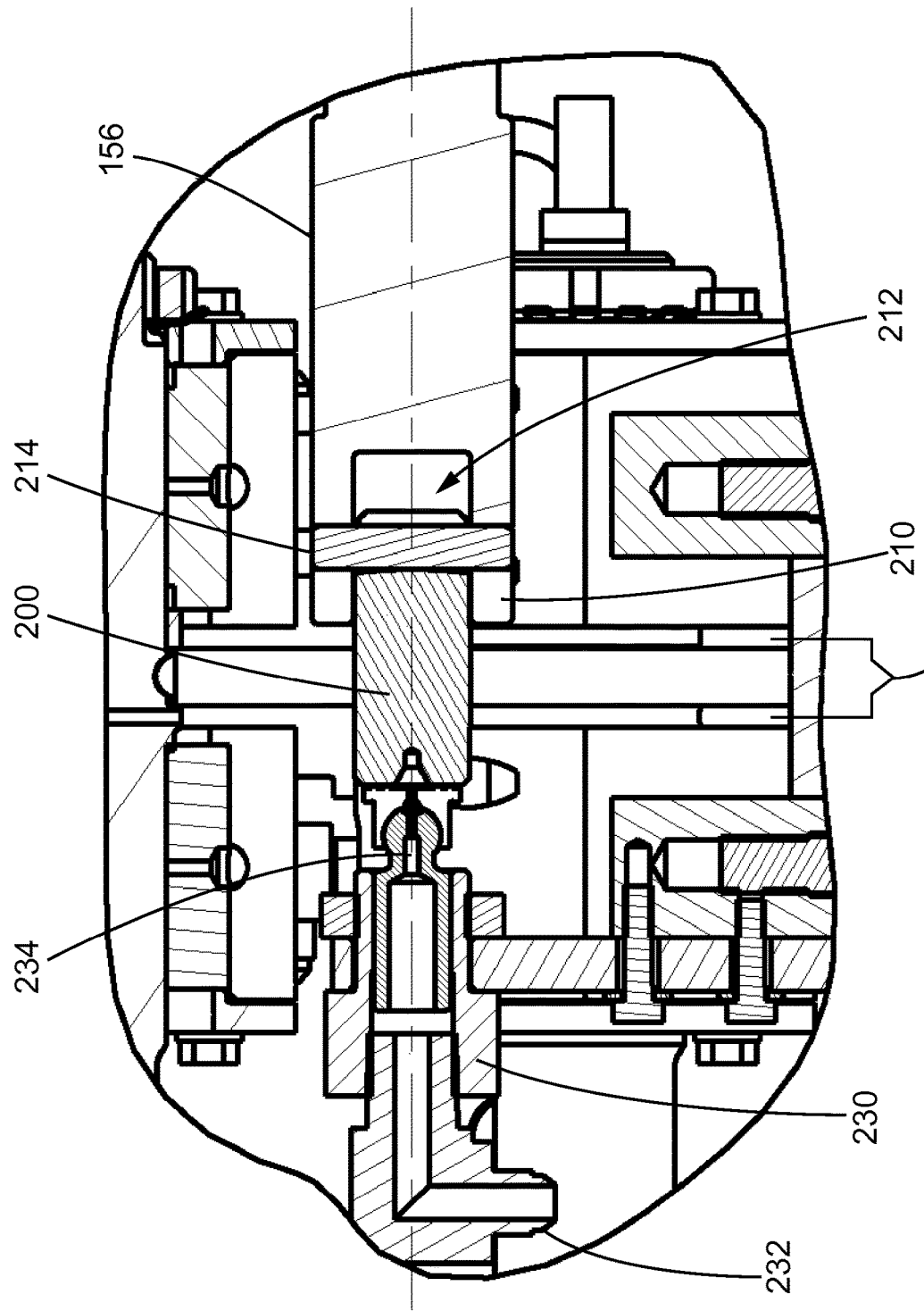
FIG. 7 is a detailed view of the area indicated in FIG. 4 showing a configuration for introducing lubricant between the three load rollers and the test roller.

Referring to FIGS. 6 and 7, to selectively remove and replace the test roller 200 from the test unit 130, for example, to carry out visual inspection of the test roller or when switching test pieces, the test roller can be releasably coupled to the second roller shaft 156 extending into enclosure 140. In particular, the second roller shaft 156 approaches the load roller arrangement 160 from the second sidewall 144. To accommodate the test roller 200, the distal end 210 of the second roller shaft 156 directed toward the load roller arrangement 160 can include a bore or cavity 212 disposed axially into the second roller shaft. The cavity 212 can have a complementary shape to and dimension with the test roller 200 such that the test roller can be slidably received in the cavity. A pin 214 can also be inserted through a corresponding series of aligned apertures disposed radially through the distal end 210 and the test roller 200 to lock the components together similar to a clevis. Dislodging the pin 214 releases the test roller from the distal end 210 of the second roller shaft 156.

Because the test roller 200 is coupled to the second roller shaft 156 that, in turn, is coupled to the second drive unit through the second drive flange 152, it will be appreciated that the test roller can be selectively rotated with respect to the load roller arrangement 160 by operation of the second drive unit. Referring to FIG. 5, it can be appreciated that by rotating the test roller 200 in synchronous speed or at the same rotational speed, measured for example in revolutions-per-minute (RPM), with the first, second, and third load rollers 162, 164, 166, the test roller and load rollers will be in pure rolling contact. Under such conditions, it will be further appreciated that the first, second, and third load rollers 162, 164, 166 and the test roller 200 are applying normal loads against each other. However, if the speeds of rotation are different between the loading and test rollers, sliding contact occurs in which the first, second, and third peripheral surfaces 170, 172, 174 of the three load rollers and the cylindrical exterior surface 202 of the test roller will be in sliding contact wherein the surfaces slide with respect to one another. Accordingly, by varying the relative speeds of the rollers, the wear testing machine can simulate different rolling and sliding conditions. In an alternative embodiment, it may be possible to replace the second drive unit with a brake to vary the relative rotational speeds between the load and test rollers.

Referring to FIGS. 2 and 5, to facilitate placement of the test roller 200 in the load roller arrangement 160, the load arm 190 can be configured to articulate with respect to the load roller assembly. In particular, a pivoting end 220 of the load arm 190 can be pivotally attached by a pivot point 222 to an upright 224 that is vertically arranged in the enclosure 140 adjacent to one edge of the load roller arrangement. An articulating end 226 of the load arm 190 opposite the pivoting end 220 can connect to a hydraulic cylinder 228 that is vertically arranged on the opposite edge of the load roller arrangement 160. Moreover, as illustrated in FIG. 5, the hydraulic cylinder 228 can vertically extend and retract with respect to the load roller arrangement 160 so as to lift the load arm 190 from a position lying horizontally over the load roller arrangement to the position indicated in dashed lines. Because the load arm 190 is operatively connected with the first load roller 162, it can carry or lift the first load roller from the load roller arrangement 160 thereby freeing the test roller 200 for removal from the wear testing machine.

Continuing to refer to FIG. 5, to increase the load applied by the roller arrangement 160 to the test roller 200, the hydraulic cylinder 228 can be vertically refracted thereby pulling the load arm horizontally against the roller arrangement. This motion pulls the upper first load roller 162 against the lower second and third load rollers 164, 166 compressing the test roller 200 disposed between the three load rollers. Accordingly, actuation of the hydraulic cylinder 228 can increase or decrease the compressive load being applied to the test roller 200 at the three points of contact thereby enabling further variation in the testing characteristics and conditions of the wear testing machine. The hydraulic cylinder 228 can have any suitable size and/or force outputs required for the desired testing. Moreover, the hydraulic cylinder can extend and retract in an alternating manner to cycle the loading conditions on the test roller similar to the intended loading applications of, for example, engaged gears.

To facilitate testing of lubricants with the wear test machine, the machine can be configured to supply lubricants such as oil or grease to the points of contact between the load rollers and test roller. For example, referring to FIGS. 6 and 7, a nozzle 230 can be disposed at a fixed location in the spacing between the three load rollers proximate to the testing roller 200. The nozzle 230 can include a port 232 connectable to a lubricant supply hose or tubing communicating with a lubricant supply and can include one or more orifices 234 directed at the portion of the test roller 200 protruding from the distal end 210 of the second roller shaft 156. When pressurized lubricant is delivered to the nozzle 230, it can be sprayed from the orifice or orifices 234 over the cylindrical exterior surface 202 of the test roller 200.

In another alternative embodiment, lubricant can be supplied to the peripheral surface of the load rollers for transfer to the contact points. For example, referring to FIG. 6, a hollow axial passage 240 can be disposed axially into the first load roller 162 partially along its length that communicates with a radial passage 242 also disposed in the first load roller. The radial passage 242 also protrudes through to the peripheral surface of the first load roller 162. The axial passage 240 can also communicate with a rotary union 244 or the like disposed at a face of the first load roller that, in turn, communicates with a lubricant supply. Accordingly, when the first load roller 162 is rotating, lubricant supplied to the axial passage 240 will be directed by centrifugal force through the radial passage 242 to the peripheral surface of the load roller. The lubricant can form a film or coating over the rollers to simulate boundary or full film lubrication conditions. By adjusting the pressure and/or volume of lubricant delivered, the lambda ratio representing the ratio of the fluid thickness to the surface roughness can be likewise adjusted.

INDUSTRIAL APPLICABILITY

In accordance with an aspect of the disclosure, a wear testing machine simulates the conditions moving parts such as, for example, engaging gears may be subjected to in a variety of different applications. The wear testing machine can be experimentally utilized to study and assess any suitable tribology topic such as surface roughness effects, surface treatments, lubricant qualities, friction and wear resistances of materials, etc. Referring to FIGS. 2 and 5, to experiment with the wear testing machine, the load arm 190 is lifted by the pneumatic cylinder 228 and the test piece in the form of the test roller 200 is positioned in a load roller arrangement 160 including at least a first, second, and third load roller 162,164, 166. When the load arm 190 is lowered, the three load rollers 162,164, 166 can be arranged in a fixed, triangular layout 186, as indicated by the dashed triangle, generally disposed around and making at least three points of contact with the test roller 200.

During testing, as indicated by the arrows 188, the three load rollers 162,164, 166 can rotate in position with respect to each other and with respect to the test roller 200 that, due to the contact therebetween, can impart a counter-rotating motion to the test roller as indicated by arrow 208. Accordingly, the test roller 200 can be in continuous, moving contact with the three load rollers 162,164, 166. In some embodiments, the test roller 200 can be operatively coupled to a second drive unit and can be rotated independently with respect to the three load rollers. Having the three load rollers and the test roller arranged for independent rotation relative to each other facilitates a range of rolling, sliding, or slipping motions between the surfaces of the load and test rollers that the wear testing machine can produce.

Moreover, the testing unit 130 of the wear testing machine 100 can subject the test roller to and alter various test conditions. For example, the compressive load applied by the load roller arrangement 160 to the test roller 200 can be set to any desired level and can be increased or decreased during testing by the respective retraction or extension of the hydraulic cylinder 228. In different embodiments, the wear testing machine 100 can lubricate the surfaces of the interacting load and test rollers by, for example, spraying a pressurized lubricant from nozzles toward the points of contact or by coating the surfaces with a lubricant supplied internally from the rollers. In addition, in various embodiments, the temperature, humidity, or other conditions inside the testing unit 130 can be adjustably controlled to simulate temperatures of an intended application. Depending upon the properties being assessed by the test, the test roller 200 can be run continuously within the load roller arrangement 160 until failure or can be run for a predetermined duration and removed for inspection. For example, visual inspection of the cylindrical exterior surface 202 of the test roller 200 can indicate the suitability of different lubricants for different applications. Sensors and electronic monitors disposed about the test unit 130 can communicate with components like the hydraulic cylinder and the drive units to provide further information to assist in testing.

Among the possible advantageous of the wear testing machine is that the three points of contact between first, second, and third load rollers 162,164, 166 and the test roller 200 can speed the testing process. For example, because the three load rollers 162,164, 166 will, in combination, contact any given point around the cylindrical exterior surface 202 of the test roller 200 three times for each revolution of the test roller. The impact events and loading conditions are accordingly multiplied per unit time to increase wear rate as compared with another wear testing device that produces a single point of contact with a test piece. The disclosed wear testing device is capable of simulating low speed, high load conditions such as tribology testing of intermeshing gears but can also simulate other conditions and applications.

Moreover, the three points of contact occurring equidistantly about the test roller 200 supports the test roller and can avoid unintentional bending or deflection of the second roller shaft 156 supporting the test roller. Another advantage possible in embodiments having first and second drive units is that the relative speed between the first, second, and third load rollers 162,164, 166 and the test roller 200 can be adjusted over a wide range, thereby simulating different degrees of rolling, sliding, or slippage. Another possible advantage is that different loads and lubrication can be applied to the test roller. These and other advantages should be apparent from the foregoing description and the accompanying drawings.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

We claim:

1. A wear testing machine comprising:
    a plurality of load rollers cylindrical in shape including at least a first load roller, a second load roller, and a third load roller;
    the first load roller, the second load roller and the third load roller disposed in a triangular layout with each other;
    the first load roller, the second load roller, and the third load roller each rotatable around a respective axis line;
    a test roller cylindrical in shape disposed between and in simultaneous contact with the first load roller, the second load roller, and the third load roller;
    the test roller being rotatable with respect to the plurality of load rollers; and
    a lubricant supply system for pressurizing a lubricant and directing the lubricant to the exterior surface of at least one of the first load roller, second load roller, third load roller, and test roller during rotation of the load rollers and test roller;
    wherein the second load roller and the third load roller are supported in bearing blocks and the first load roller is supported by a load arm extending over the second load roller and the third load roller.

2. The wear testing machine of claim 1, wherein the load arm extends between an articulating end and a pivoting end, the pivoting end pivotally connected to the wear testing machine and the articulating end connected to a hydraulic cylinder.

3. The wear testing machine of claim 1, wherein the first load roller, the second load roller, and the third load roller are configured to rotate at a same rotational speed as the test roller.

4. The wear testing machine of claim 3, wherein the first load roller, the second load roller, and the third load roller are configured to rotate at a different rotational speed as the test roller.

5. The wear testing machine of claim 4, wherein the first load roller, the second load roller, and the third load roller are configured to selectively switch rotation between the same rotational speed as the test roller and the different rotational speed as the test roller.

6. The wear testing machine of claim 1, wherein the lubricant supply system further includes at least one spray nozzle disposed to spray lubricant toward the test roller and/or the plurality of load rollers.

7. The wear testing machine of claim 1, wherein the lubricant supply system further includes at least one lubricant supply passage disposed in the first load roller to supply lubricant to a peripheral surface of the first load roller.

8. The wear testing machine of claim 1, wherein the plurality of load rollers and the test roller are disposed in a test unit, the test unit including an enclosure having a first sidewall and a second sidewall opposing the first sidewall.

9. The wear testing machine of claim 8, further comprising a first drive motor disposed outside the first sidewall operatively coupled to the plurality of load rollers.

10. The wear testing machine of claim 9, wherein the first load roller, the second load roller, and the third load roller are configured for synchronous rotation with respect to each other via a gear train disposed in the enclosure.

11. The wear testing machine of claim 8, further comprising a second drive motor disposed outside the second sidewall that is operatively coupled to the test roller, wherein the test roller is releasably coupled to a shaft protruding into the enclosure.

12. A method of wear testing comprising:
    providing a load roller arrangement including a first load roller, a second load roller, and a third load roller in a triangular layout, the first load roller configured to articulate with respect to the second load roller and the third load rollers;
    disposing a test roller between and in contact with the first load roller, the second load roller, and the third load roller with at least three points of contact;
    rotating the first load roller, the second load roller, and the third load roller with respect to the test roller, and
    pressurizing a lubricant from lubricant supply system and directing the lubricant to the exterior surface of at least one of the first load roller, the second load roller, the third load roller, and the test roller during rotation of the load rollers and test roller;
    wherein the second load roller and the third load roller are supported in bearing blocks and the first load roller is supported by a load arm extending over the second load roller and the third load roller.

13. The method of claim 12, further comprising rotating the first load roller, the second load roller, and the third load roller at a same rotational speed of the test roller to induce rolling contact.

14. The method of claim 12, further comprising rotating the first load roller, the second load roller, and the third load roller at a different rotational speed of the test roller to induce sliding.

15. The method of claim 12, further comprising applying a load to the test roller by articulating the first load roller with respect to the second load roller and the third load roller.

16. A wear testing machine comprising:
- a load roller arrangement, the load roller arrangement including a plurality of load rollers configured to rotate about a respective plurality of axis lines;
- a test roller disposed partially within the load roller arrangement, the test roller making at least three points of contact with the plurality of load rollers of the load roller arrangement; and
- a lubricant supply system for pressurizing a lubricant and directing the lubricant to the exterior surface of at least one of the first load roller, the second load roller, the third load roller, and the test roller during rotation of the load rollers and test roller;
- wherein the second load roller and the third load roller are supported in bearing blocks and the first load roller is supported by a load arm extending over the second load roller and the third load roller.

17. The wear testing machine of claim 16, wherein the plurality of load rollers are arranged in a triangular layout.

* * * * *